United States Patent [19]

Thurston et al.

[11] Patent Number: 5,427,095
[45] Date of Patent: Jun. 27, 1995

[54] METHOD AND APPARATUS FOR DETECTING CATARACTOGENESIS

[75] Inventors: George M. Thurston, Belmont; Douglas L. Hayden, Cambridge; George B. Benedek, Belmont, all of Mass.

[73] Assignee: Massachusetts Institute of Technology Oculon Corporation, Cambridge, Mass.

[21] Appl. No.: 149,353

[22] Filed: Nov. 9, 1993

[51] Int. Cl.6 .............................................. A61B 5/00
[52] U.S. Cl. .................................. 128/633; 128/653.1; 128/645; 128/664; 128/665; 607/89
[58] Field of Search .................... 128/653.1, 633, 645, 128/664, 665; 607/88, 89

[56] References Cited

U.S. PATENT DOCUMENTS

| | | | |
|---|---|---|---|
| 4,350,163 | 9/1982 | Ford, Jr. et al. | 128/633 |
| 4,702,576 | 10/1987 | Magnante | 351/214 |
| 4,854,693 | 8/1989 | Ichihashi et al. | 128/653.1 X |
| 4,957,113 | 9/1990 | Benedek | 128/665 |
| 5,072,731 | 12/1991 | Taratuta et al. | 128/633 |
| 5,203,328 | 4/1993 | Samuels et al. | 128/633 |
| 5,258,788 | 11/1993 | Furuya | 128/633 |
| 5,279,296 | 1/1994 | Thurston et al. | 128/633 |
| 5,318,022 | 6/1994 | Taboada et al. | 128/633 |

FOREIGN PATENT DOCUMENTS

| | | | |
|---|---|---|---|
| 2112171 | 7/1983 | United Kingdom | A61B 3/10 |
| WO92/11799 | 7/1992 | WIPO | A61B 3/117 |

Primary Examiner—Lee S. Cohen
Assistant Examiner—Brian L. Caster
Attorney, Agent, or Firm—Seed and Berry

[57] ABSTRACT

A method and an apparatus are disclosed for using quasielastic light scattering to determine the degree of cataractogenesis of a lens in vivo. By collecting and analyzing light scattered from the lens, it is possible, using the temporal autocorrelation function, to produce a signature of cataractogenesis, accounting for scattering due to substantially immobile scatterers. The component of the temporal autocorrelation function representing the effect of the substantially immobile scatterers is expressed as a function of the measurement delay time. The components of the cataractogenesis can also be detected by comparing the values of the components of the signature of cataractogenesis to frequency distribution of the components taken from populations or by detecting changes in the values of the components of the signature of cataractogenesis as a function of time.

16 Claims, 3 Drawing Sheets

METHOD AND APPARATUS FOR DETECTING CATARACTOGENESIS

TECHNICAL FIELD

The present invention relates to a method and apparatus for detecting diseases, and more particularly, to a method and apparatus for detecting diseases by inspecting ocular tissue.

BACKGROUND OF THE INVENTION

A reliable, quantitative and non-invasive method for the characterization of the molecular changes associated with early cataractogenesis in vivo has long been an important goal of human clinical cataract research. Such a method would allow researchers and physicians to (a) assess the effectiveness of putative anticataract reagents; (b) evaluate the cataractogenic role of pharmacologic agents or radiation used in the treatment of systematic diseases; (c) characterize early cataract in epidemiologic studies of human or animal populations subject to differential cataractogenic stress; and (d) provide a quantitative basis for the medical decision to intervene surgically or pharmaceutically in the treatment of cataract.

In 1975, T. Tanaka and G. Benedek ("Observation of Protein Diffusivity in Intact Human and Bovine Lenses with Application to Cataract," *Invest. Opthal.* 14:449–456, 1985) showed that the Brownian motion of proteins in excised human and bovine lenses could be measured optically using the method of quasielastic light scattering (QLS) spectroscopy. Following this work, T. Tanaka and C. Ishimoto ("In Vivo Observation of Lens Protein Diffusivity in Normal and X-Irradiated Rabbit Lenses," *Exp. Eye Res.* 39:61–68, 1984) demonstrated that QLS could be used in vivo in rabbits to detect changes in mean protein diffusivity as a function of age and position in the rabbit ocular lens. Further observations showed that the cataractogenic insult of x-irradiation upon the rabbit lens produced dramatic changes in the form of the autocorrelation function of the scattered light at a very early stage in the cataractogenic process. The autocorrelation function is an important tool for mathematical analysis of QLS. This change in the autocorrelation function demonstrated that the x-irradiation was responsible for drastic changes in the diffusivity of the protein scattering elements undergoing Brownian movement within the ocular tissue. Both Nishio and the 1977 Tanaka team observed that these altered correlation functions had a form different from that expected for the Brownian motions of a single-type scatterer. However, neither understood a quantitative analysis of the information contained in the non-exponential character of the autocorrelation function observed.

In 1986, T. Libondi et al. ("In Vivo Measurement of the Aging Rabbit Lens Using Quasielastic Light Gathering," *Curr. Eye. Res.* 5(6):411–419, 1986) showed that the form of the autocorrelation function of the scattered light from a living rabbit eye indicated the presence of at least two distinct diffusing aspects within the rabbit lens. One species had a diffusivity corresponding to the α-crystalline protein. The other was a much more slowly diffusing species of the type discovered in vitro by M. Delaye et al. ("Identification of the Scattering Elements Responsible for Lens Opacification in Cold Cataracts," *Biophys. J.* 37:647–656, 1982).

In recent years QLS has been used to study the ocular lens in vivo and in vitro. A method and apparatus for analyzing QLS is described in U.S. Pat. No. 4,957,113, and U.S. Pat. No. 5,072,731, respectively, which are incorporated herein by reference.

The techniques described in the above-reference patents are capable of quantitating the amount of light scattered by diffusing chemical species in a medium, as well as their rates of diffusion. With QLS, the temporal fluctuations in intensity of light scattered by a selected small volume in the lens which is illuminated by an incident laser beam are studied. The scattered light intensity fluctuates in time because of the Brownian motion of the scattering elements. Brownian motion is defined as the motion of macromolecules caused by thermal agitation and the random striking by neighboring molecules in a solution. In the lens of the human eye, the Brownian of protein molecules may be recorded and analyzed by quasielastic light scattering.

Research has shown that the principal scattering elements within the lens are the molecular constituents of the fiber cells. These constituents are principally globular proteins called crystallins. The aggregation of small proteins within the lens is the very first stage in the process of cataractogenesis. As the light scattering becomes more pronounced, it becomes noticeable to the clinician and is termed a cataract. However, this represents a late stage of a continuous process of increase in light scattering with time within the lens. By using information obtained from the light scattered by the various fast and slow moving protein species, it is possible to determine the degree of aggregation and thus the degree of cataractogenesis before it would be noted clinically.

The intensity fluctuations of the scattered light are detected by collecting the light scattered from the illuminated volume in the eye lens and focusing this light onto the surface of an optical square law detector such as a photomultiplier tube or solid-state photodiode. The output of the detector is a photoelectric current whose temporal fluctuations are synchronized with the fluctuations in the scattered light intensity. The temporal fluctuations in the photoelectric current can be mathematically analyzed to provide a quantitative measure of the degree of cataractogenesis.

The experimental data is typically expressed in the form of the temporal autocorrelation function, $C(\tau)$, of the intensity of the detected scattered light from the medium as a function of the delay time, $\tau$. From the mathematical form of the autocorrelation function of the photoelectric current, it is possible to determine the diffusivity of the scattering elements undergoing Brownian movement. The decoded information has been shown clinically to provide an accurate quantitative measure of the source of increased light scattering on a molecular level long before cataract formation could be detected visually by either the subject or the physician.

The QLS inventions described in the above-referenced patents have provided tools to detect cataract formation at a very early stage. However, it has been determined that in situations where the lens contains a significant amount of immobile proteins, these methods do not produce results that are as accurate as desired. Therefore, it can be appreciated that there is a significant need for a method and apparatus that can produce results having the desired accuracy even in a lens containing immobile proteins. The present invention fulfills this need and provides other related advantages.

SUMMARY OF THE INVENTION

The present invention is embodied in an apparatus for the in vivo detection of cataractogenesis in ocular tissue. The system includes a light source that impinges upon the ocular tissue, the light detector collecting light that is scattered from the ocular tissue, with the scattered light having a fluctuating intensity. An analyzer performs correlation analysis on the fluctuating intensity to produce a signature containing a component representing the intensity of light scattered by substantially immobile scatterers in the ocular tissue as it affects the delay time dependence of the correlation function in a non-constant fashion. The apparatus also includes means for determining the degree of cataractogenesis from the signature.

The analyzer may comprise an autocorrelator computing a temporal autocorrelation function of the intensity fluctuations. In one embodiment, the autocorrelator performs a least squares analysis on the temporal autocorrelation function to determine the functional form of the function $C(\tau)$ which best fits the temporal autocorrelation function where $$C(\tau) = \alpha[I_{mof}e^{-\tau/\tau_f} + I_{mos}e^{-\tau/\tau_s} + I_{imm}]^2 + [I_{tot}]^2,$$

where $\tau$ is a time delay variable, $\alpha$ denotes an amplitude to baseline ratio, $I_{mof}$ represents the intensity of light scattered by mobile, fast diffusing scatterers, $I_{mos}$ represents the intensity of light scattered by mobile, slowly diffusing scatterers, $I_{imm}$ represent the intensity of light scattered by light scatterers which diffuse very slowly in comparison to the mobile scatterers, $\tau_f$ and $\tau_s$ are time constants that characterize the fast and slowly diffusing scatterers, respectively, and $I_{tot}$ denotes the total, average intensity of scattered light.

Alternatively, the autocorrelator performs a least squares analysis on the temporal autocorrelation function to determine the functional form of the function $C(\tau)$ which best fits the temporal autocorrelation function, where $$C(\tau) = \alpha B\{(1-F_{imm})[(1-F_{mos})e^{-\tau/\tau_f} + F_{mos}e^{-\tau/\tau_s}] + F_{imm}\}^2 + B,$$

where $\tau$ is a time delay variable, $\alpha$ denotes an amplitude to baseline ratio, B denotes a baseline value, $F_{mos}$ denotes the fraction of light intensity scattered by mobile scatterers which is associated with slowly diffusing scatterers, $F_{imm}$ denotes the fraction of total light intensity scattered due to light scatterers which diffuse very slowly in comparison to the mobile scatterers, and $\tau_f$ and $\tau_s$ are time constants that characterize the fast and slowly diffusing scatterers, respectively.

The inventive method involves producing a light, causing the light to impinge upon the ocular tissue, and collecting light that is scattered from the ocular tissue, with the scattered light having fluctuating intensity. The method further involves performing a correlation analysis on the fluctuating intensity to produce a signature containing a component representing the intensity of light scattered by substantially immobile scatterers in the ocular tissue as it affects the delay time dependence of the correlation function in a non-constant fashion. The degree of cataractogenesis is determined from the signature.

DETAILED DESCRIPTION OF THE INVENTION

The present invention provides a new signature that is useful in the detection of cataractogenesis in a lens having very slowly diffusing proteins that are substantially immobile in the ocular tissue within the range of delay times assayed. As will be discussed below, the mathematics for analyzing the diffusion of the very slowly diffusing proteins may be taken to a mathematical limit describing the very slow diffusion relative to the other scattering components.

Previous work has indicated the need to account for light scattering due to substantially immobile scatterers. Such work is described in U.S. Pat. No. 5,279,296, incorporated herein by reference.

In a subsequent U.S. patent application Ser. No. 948,272, filed Sep. 21, 1992, and incorporated herein by reference, it is reported that the cataractogenesis can be further determined with the use of a dimensionless parameter, $F_{mos}$, which denotes the fraction of light intensity scattered by mobile scatterers which is associated with slowly moving scatterers.

As discussed above, the fluctuating scattered light intensity is detected and expressed as an autocorrelation function. The autocorrelation function may be determined by using an autocorrelator to analyze the fluctuations in the intensity of the laser light scattered by the ocular tissue. The random motions of the crystalline proteins within the lens give rise to concentration fluctuations, which in turn give rise to fluctuations in the intensity of the scattered light. This scattered light may be recorded in the form of a time correlation function, the autocorrelation function $C(\tau)$, which relates the scattered light intensity at a time t, I(t), to the scattered light intensity a certain time $\tau$ later, I(t+$\tau$), as follows: $C(\tau) = <I(t)I(t+\tau)>$, where $<>$ denotes averaging over all starting times t.

Figure 1:
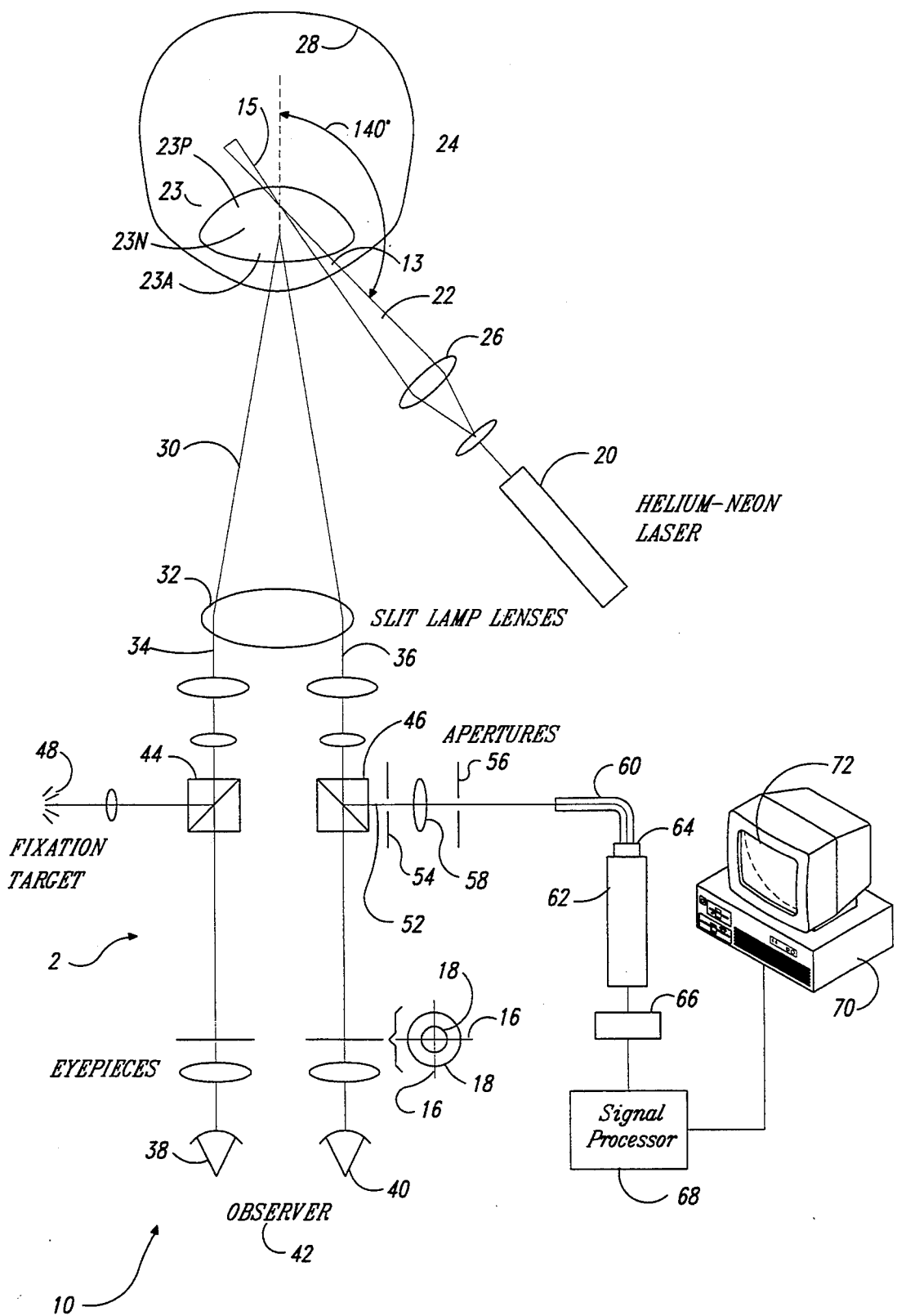
FIG. 1 is a schematic representation of an optical scattering analyzer for the study of the intensity and temporal fluctuations of the intensity of laser light scattered from the lens in vivo.

Turning now to the figures, FIG. 1 is a schematic representation of an optical scattering analyzer for the study of the temporal fluctuations of laser light scattered from a lens in vivo. A preferred embodiment of the inventive system 10 is shown in FIG. 1, where a source of substantially monochromatic, coherent, collimated light 20, such as a laser, delivers a light beam 22, to the lens 23 of a subject's eye 24, through a delivery means, which may consist of, for example, a focusing lens 26 which serves to focus the light beam 22 onto the subject's eye 24 at the specific location at which the measurement is to be taken. The light must be focused for two reasons. First, the size of the illuminated area is inversely proportional to the coherence area of the scattered light. By focusing onto a small area, a greater coherence area is obtained which allows easier measurement. Second, the incident contact area on the lens 23 is inversely proportional to the scattering area on the retina 28. There are three areas of the lens 23 that are of particular interest. They are the anterior cortex 23a, the posterior cortex 23p and the nucleus 23n. By focusing on the lens 23, the light going to the retina 29 is diffused, thereby preventing retinal damage. Scattered light 30 from the eye lens 23 passes through a collector 32 such as an objective lens. The scattered light 30 is split into two light beams 34 and 36, which are respectively directed to the left and right eyes 38 and 40 of an observer 42. The light beams 34 and 36 respectively pass through beam splitters 44 and 46. A light from an adjustable fixation target 48 is directed through the beam splitter 44 to help fix the position of the individual subject's eye 24 as measurements are being made. As can be appreciated, a portion of the scattered light 30 also passes through the beam splitter 44 and is directed to the adjustable fixation target 48. The remainder of the beam that is split by the beam splitter 44 is directed toward the left eye 38 of the observer 42.

The light beam 36 is split by the beam splitter 46 into one portion 50 which passes directly to the right eye 40 of the observer 42 and a second portion 52 which passes through apertures 54 and 56, and is focused by the lens 58 onto the end of the optical fiber 60. The apertures 54 and 56 limit the length of the light beam 52. The optical fiber 60 directs the light beam 52 to an optical square law detector 62, such as a photomultiplier tube or solid-state photodiode, after passing through an optical filter 64. The light passing into the optical square law detector 62 is converted into a photoelectric signal through the optical filter 64, such as a photomultiplier tube or solid-state photodiode. The signal from the optical square law detector 62 is pre-processed by an amplifier and discriminator 66. This signal is then inputted into a signal processor 68 (which can be a standalone autocorrelator or a programmed computer), and a computer 70 for processing as discussed previously. The computer 70 can be a programmed microprocessor or an integral circuit. The autocorrelation function and any calculated parameters can be shown on a display 72.

In operation, a slit lamp biomicroscope 12, such as one manufactured by Topcon was modified to incorporate the laser light source 20 and photoelectric detection of the light scattered from the eye. The patient gazes at the adjustable fixation target 48 built into one of the optical paths of the binocular microscope. The helium-neon laser beam 22 is incident on the eye 24, with an intensity of 160 microwatts during each 10-second measurement, and an intensity of 30 microwatts during alignment. The direction of the incident beam forms an angle of 140° with the axis of the detection optics. The beam is focused to a diameter of approximately 15 microns within the ocular lens 23, and subsequently diverges before reaching the retina 28. The stated power levels and geometry ensure that the laser power incident upon the retina 28 is within the American National Standards Institute Guidelines for the Safe Use of Lasers.

The scattering measurement volume within the lens 23 consists of a 300 micron length of the 15 micron diameter beam. Scattered light emerging from the lens 23 is incident upon the end of the fiber-optic cable 60, which carries the light to the photon-counting photomultiplier tube 62, such as one manufactured by E.M.I. Electro-Optics. The amplifier-discriminator 66, which may be a commercially available instrument, such as one manufactured by Pacific Precision Instruments, shapes the emerging pulses, and a computing autocorrelator 68, such as one manufactured by Malvern Instruments, is set to use 128 serial, 10 microsecond channels, to make a digital estimate of the temporal autocorrelation function of the intensity of the scattered light 30. An additional 8 channels, starting at 5.1 milliseconds, are used to estimate a delayed point. For each measurement, the correlation function is collected for 10 seconds. The average total intensity, $I_{tot}(140)$, is obtained from the total number of pulses detected. Alternative correlator set-ups may also be used with the present invention.

Figure 2:
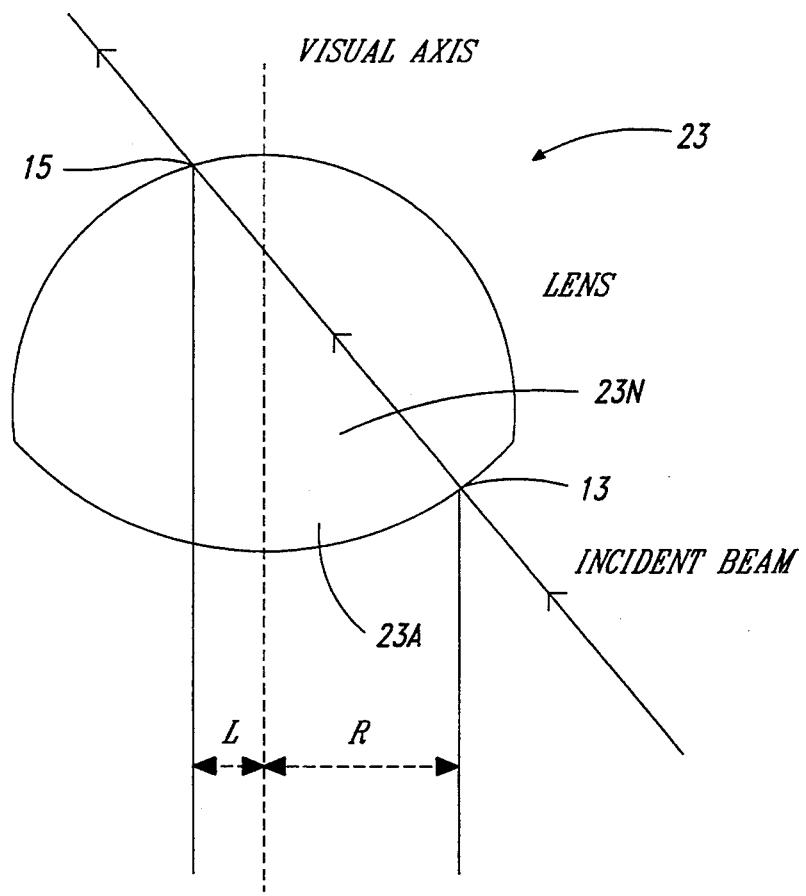
FIG. 2 illustrates the technique used by the system of FIG. 1 to determine the location of the scattering volume within the ocular lens.
Figure 3A:
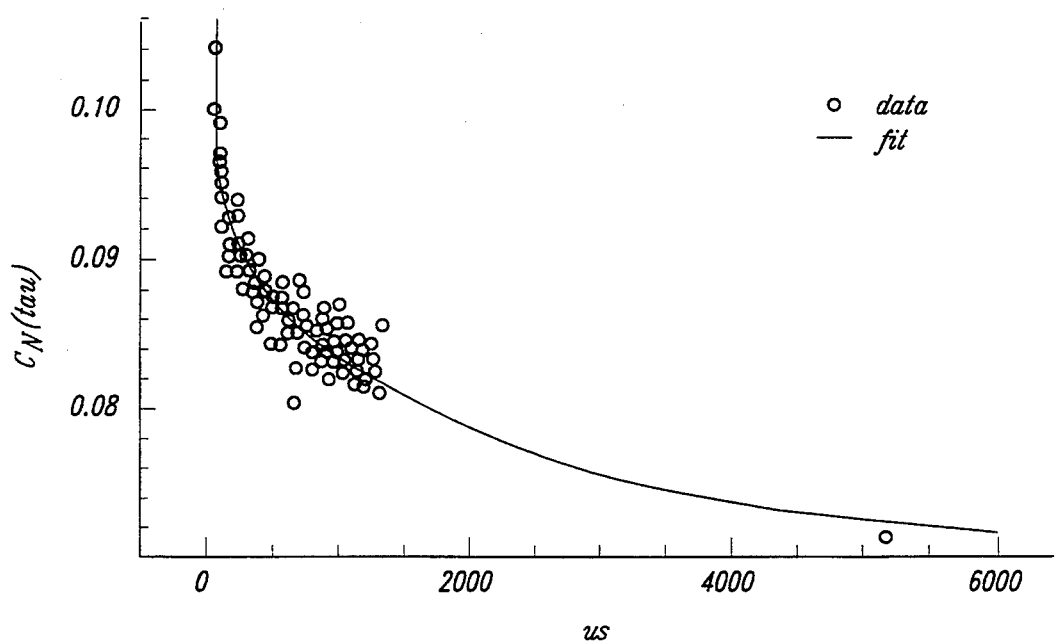
FIG. 3A is a graph of the data using the instrument of FIG. 1 and fit to the autocorrelation function of the present invention.
Figure 3B:
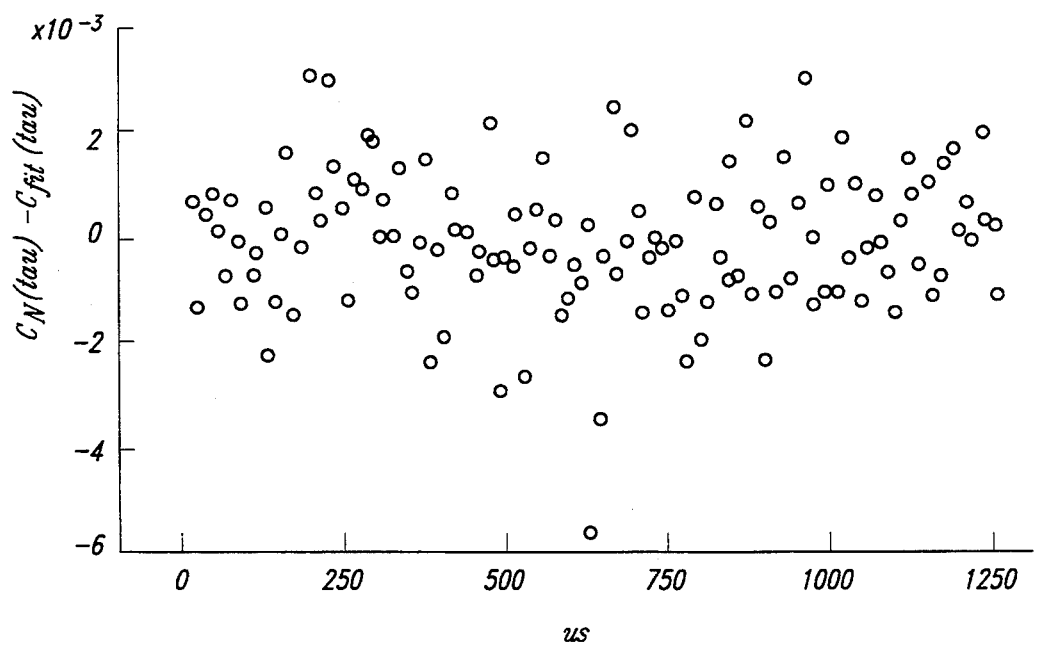
FIG. 3B is a graph of the residual data resulting from the curve fitting of the data of FIG. 3A to the autocorrelation function of the present invention.

The operator views the light beam 22 through the slit lamp binocular 12 and positions the desired scattering measurement volume within the lens 23. For this purpose, an eyepiece reticule 14 is used which is ruled with a cross-hair 16 and with concentric, evenly spaced circles 18. The position of the cross-hair 16 corresponds with the center of the scattering measurement volume 19. The concentric circles 18 are used both to center the measurement volume 19 in the iris and to quantitate the anterior to posterior position of the measurement volume 19 in the lens 23. The position was quantitated by observing the image of the entire transversal of the lens by the incident laser beam 22. The positions of the entry 13 and exit 15 of the light beam 22 to and from the lens 23 are seen superimposed on the concentric circles 18, thereby quantitating their distances R and L from the measurement axis of the portion 50. The distances, R and L, are used to provide an estimate, $l=R/(R+L)$, of the fractional depth, $l$, of the measurement volume in the lens, as shown in FIG. 2. As can be appreciated, this calculation provides only an estimate of the fractional depth, $l$, of the measurement volume. A value of 0.5 indicates that the measurement volume is approximately in the nucleus 23n of the lens 23. More accurate estimates of the location within the lens can be made which account for the optical and geometic consequences of the curvature and refractive indices of the cornea aqueous and lens.

As a further improvement, a model form of the autocorrelation function has been developed in the present invention to more accurately represent the interaction of the various species of light scattering elements. The new model form of the autocorrelation was developed based on a study of QLS used for in vivo examination of the ocular lenses of 225 subjects ranging from 17 to 63 years of age. Light scattered at 140° from an incident of 632.8 nm wavelength laser beam was detected and used to compute the temporal autocorrelation function of the scattered intensity up to delay times of 1.3 ms, with an additional point at 5.2 ms. The intensity fluctuations are well described by fast and slow diffusing components with diffusivities $D_f = 2.5$ to $3.5 \times 10^{-7}$ cm$^2$/sec and $D_s = 1.5$ to $4 \times 10^{-9}$ cm$^2$/sec, respectively, together with a component that does not appreciably diffuse on this time scale. Key parameters have been determined which characterize the observed autocorrelation functions, together with their dependence on age and location along the axis of the ocular lens. These include $D_f$, $D_s$, the total light scattering intensity $I_{tot}(140)$, and the intensities of light $I_{mof}$, $I_{mos}$ and $I_{imm}$ scattered by the mobile fast, the mobile slow and the substantially immobile components, respectively. With increasing age, $I_{tot}(140)$ increases, due almost entirely to an increase in $I_{mos}$, and $D_S$ decreases. These in vivo findings help quantitate the increased association of protein in the lens cytoplasm with age.

The study population, shown in Table 1, consisted of 225 subjects between ages 17 and 63. Bone marrow transplant patients, healthy bone marrow transplant donors, and paid normal volunteers were included, with one measurement session each. Patients had not received total body irradiation or steroid treatment. Subjects with prior history of steroid use were excluded.

TABLE 1

Study composition by age, gender, and subject category.

| Age (years) | Patients | | Donors | | Volunteers | | All* |
|---|---|---|---|---|---|---|---|
| | F* | M* | F | M | F | M | |
| <20 | 0 | 2 | 0 | 1 | 0 | 0 | 3 |
| 20 to 30 | 5 | 14 | 7 | 11 | 16 | 1 | 54 |
| 30 to 40 | 19 | 21 | 13 | 10 | 7 | 4 | 74 |
| 40 to 50 | 7 | 21 | 9 | 5 | 6 | 3 | 51 |
| 50 to 60 | 10 | 14 | 3 | 7 | 3 | 0 | 37 |
| >60 | 0 | 1 | 2 | 2 | 1 | 0 | 6 |
| Totals | 41 | 73 | 34 | 36 | 33 | 8 | 225 |

*F = female;
M = male;
All = total

After fully dilating the pupils, measurements were taken in the anterior cortex, nucleus, and posterior cortex of the lens of each eye, along the visual axis. Light scattering intensities from each location were also graded by the instrument operator on a 0 to 4+ scale. Measurement sessions consisted of a total of 8 to 28 measurements, some of which were repeated.

In the presently preferred embodiment, the autocorrelation functions $C(\tau)$ obtained from the autocorrelator 68 are the sums $$C(\tau) = \sum_{i=1}^{(T/\delta t)} n(i)n(i - (\tau/\delta t)) \quad (1)$$

in which $\tau$ denotes the delay time, T is the total time of the measurement, $\delta t$ is the sample time interval within which photon counts are binned, and $n(i)$ is the number of photon counts arriving between times $t=(i-1)\delta t$ and $t=i\delta t$. In the present study, the delay time $\tau$ was set to take the evenly spaced values $\delta t, 2\delta t, \ldots 128\delta t$, followed after a delay by $513\delta t, 514\delta t, \ldots, 520\delta t$. Also in the present preferred embodiment, T=10 seconds and $\delta t = 10$ microseconds. Edge effects at the beginning and end of acquisition are neglected in the representation of equation (1) as $(T/\delta t)=10^6 >> 512$. In addition, the autocorrelator 68 determines the value of total intensity of light scattered using the following formula:

$$I_{tot} = (1/T) \sum_{i=1}^{(T/\delta t)} n(i) \quad (2)$$

in which the sum is the total number of photons detected, so that $I_{tot}$ is proportional to the total intensity of the scattered light and is the average number of photons detected per second.

Autocorrelation functions were fit to a double exponential model similar to that used previously. First, a normalized autocorrelation function, $C_N(\tau)$, was computed from the formula $$C_N(\tau) = \frac{C(\tau) - T\delta t\,(I_{tot})^2}{(T\delta t)\,(I_{tot})^2}. \quad (3)$$

In equation (3), the quantity $(T\delta t)(I_{tot})^2$ is termed the calculated baseline, and represents the value $C(\tau)$ would approach for delay times $\tau$ sufficiently large so that the values of $n(i)$ and $n(i-(\tau/\delta t))$ are uncorrelated, so long as the expected value, $E(n(i))$, is not a function of time.

The $C_N(\tau)$ so obtained, including a single delayed point representing the average of the channels starting at 5.1 milliseconds, were then fit on the computer 70 using a Marquardt nonlinear least squares fitting algorithm, such as one available from Certified Scientific Software, Cambridge, Mass.), to the model correlation function:

$$C_{fit}(\tau) = \alpha\{(1-F_{imm})[(1-F_{mos})e^{-\tau/\tau_f} + F_{mos}e^{-\tau/\tau_s}] + F_{imm}\}^2. \quad (4)$$

In equation (4), $\alpha$ denotes the amplitude to calculated baseline ratio, $\tau_f$ and $\tau_s$ are time constants which characterize the rapidly and slowly diffusing scatterers, respectively, $F_{mos}$ denotes that fraction of the light intensity scattered by mobile scatterers which is associated with the slowly diffusing scatterers, and $F_{imm}$ denotes that fraction of the total light intensity due to scatterers which are substantially immobile within the range of delay times assayed. Equation (4) is the limiting functional form of the correlation function expected to apply on theoretical grounds in the case of three types of diffusing scatterers, in the case in which one of the diffusion coefficients is very small. The new autocorrelation function of the present invention represents the contribution of light scattering by substantially immobile scatterers in a manner that affects the delay time dependence of the correlation function in a non-constant fashion. That is, the light scattering to the correlation function caused by substantially immobile scatterers is not treated as a constant.

As one can appreciate, equation (4) can be expressed in a variety of equivalent forms. For example, the following unnormalized model correlation function, not previously disclosed, is of particular use in the analysis of substantially immobile scattering from the ocular lens:

$$C(\tau) = \alpha(I_{tot})^2\{(1-F_{imm})[(1-F_{mos})e^{-\tau/\tau_f} + F_{mos}3^{-\tau/\tau_s}] + F_{imm}\}^2 + I_{tot})^2 \quad (5)$$

or alternatively $$C(\tau) = \alpha B\{(1-F_{imm})[(1-F_{mos})e^{-\tau/\tau_f} + F_{mos}3^{-\tau/\tau_s}] + F_{imm}\}^2 + B \quad (6)$$

In equations (4) to (6), $\alpha$ denotes the amplitude to calculated baseline ratio, $\tau_f$ and $\tau_s$ are time constants which characterize the rapidly and slowly diffusing scatterers, respectively, $F_{mos}$ denotes that fraction of the light intensity scattered by mobile scatterers which is associated with the slowly diffusing scatterers, and $F_{imm}$ denotes that fraction of the total light intensity due to scatterers which are substantially immobile within the range of delay times assayed. $I_{tot}$ denotes the total, average intensity of light scattered. With these definitions, $I_{imm}$, the intensity of the light scattered by scatterers which are substantially immobile within the range of delay times assayed, is given by $I_{imm} = F_{imm} I_{tot}$. Similarly, $I_{mos}$, the intensity of the light scattered by mobile, slowly diffusing scatterers, is given by $I_{mos} = I_{tot}(1 - F_{imm})F_{mos}$. $I_{mof}$, the intensity of the light scattered by mobile, fast diffusing scatterers, is given by $I_{mof} = I_{tot}(1-$ $-F_{imm})(1-F_{mos})$. With these definitions, equation (5) can also be written in the form $$C(\tau) = \alpha \{I_{mof} e^{-\tau/\tau_f} + I_{mos} 3^{-\tau/\tau_f} + I_{imm}\}^2 + (I_{tot})^2 \quad (7)$$

In equation (6), B denotes a baseline value of the autocorrelation function which may be determined by means other than equating it to the square of the average intensity $(I_{tot})^2$, as is done in equations (5) and (7), such as with use of delayed channels in the autocorrelation function acquisition, or by directly fitting B as a parameter.

Physically the forms of equations (4) to (7) result from considering a limiting case of the autocorrelation functions in the situation where there are three types of diffusing scatterers present: fast, slow and very slow (denoted by "vs"). In such a case, the homodyne autocorrelation function of the scattered intensity is well known to have the form $$C(\tau) = \alpha \{I_{mof} e^{-\tau/\tau_f} + I_{mos} e^{-\tau/\tau_s} + I_{vs} 3^{-\tau/\tau_{vs}}\}^2 + \{I_{mof} + I_{mos} + I_{vs}\}^2 \quad (8)$$

in which $I_{mof} + I_{mos} + I_{vs} = I_{tot}$. Now if the characteristic delay times $\tau_f$, $\tau_s$ and $\tau_{vs}$ are such that $\tau_{vs}$ greatly exceeds $\tau_s$, then there will be a range of the argument $\tau$ such that $C(\tau)$ in equation (8) will be very well approximated by the expression $$C(\tau) = \alpha \{I_{mof} e^{-\tau/\tau_f} + I_{mos} e^{-\tau/\tau_s} + I_{vs}\}^2 + (I_{mof} + I_{mos} + I_{vs})^2 \quad (9)$$

in which the term $e^{-\tau/\tau_{vs}}$ has been replaced by the value, "1", which is the first term in a power series expansion of $e^{-\tau/\tau_{vs}}$ in the vicinity of $\tau = 0$, the first three terms of that power series expansion being given by $$e^{-\tau/\tau_{vs}} = 1 - (\tau/\tau_{vs}) + (\tfrac{1}{2})(\tau/\tau_{vs})^2 + \ldots \quad (10)$$

With the identification $I_{vs} = I_{imm}$, we see that equation (9) is actually the algebraic equivalent of equation (7). The derivation of equation (9) as given thus provides an interpretation of the quantity $I_{imm}$ appearing in equation (7) as the intensity $I_{vs}$ scattered from scatterers which diffuse very slowly in comparison to the previously identified slowly diffusing scatterers.

Equations (4), (5), (6), and (7) are model functional forms which correspond to equation (7) or (9), via the definitions of the quantities $F_{imm}$, $F_{mos}$, and $I_{tot}$ given above. As noted above, equation (6) results from equation (5) upon relaxation of the requirement that the baseline, B, of the autocorrelation function be identified with the quantity $(I_{tot})^2$.

Clearly, if more terms in the power series expansion given in equation (10) are substituted into equation (8), corresponding alternate forms of equation (8) and corresponding alternate versions of equations (4), (5), (6), and (7) will result. Clearly, in the proper range of $\tau$ such an expansion could also be made of the term $e^{-\tau/\tau_s}$ appearing in equation (7) and in the corresponding equations.

The correlation functions of the present invention have the advantage over previous functional forms characterizing substantially immobile scattering elements that they result from a specific physical model of the scattering process as detailed in equation (8) and thus can represent the observed correlation functions in a more accurate manner.

As discussed above, the quantities $\tau_f$ and $\tau_s$ are related to the diffusivities $D_f$ and $D_s$ associated with mobile scatterers by $\tau_f = (1/D_f q^2)$ and $\tau_s = (1/D_s q^2)$, where $q = (4\pi n/\lambda)\sin(\theta/2)$, in which $\lambda$ is the wavelength of the laser beam in vacuo, 632.8 nm, n is the index of refraction of the material within the scattering volume, and $\theta$ is the angle between the directions of propagation of the incident and the scattered light. Physically $\tau_f$ and $\tau_s$ represent times for the decay of concentration fluctuations having wavelength $(2\pi/q)$. In the present instrument, $\theta = 140°$, and we take $n = 1.4$ as a suitable average value in the analysis below. This gives $q^2 = 6.83 \times 10^{10}$ cm$^{-2}$. For the typical values $\tau_f = 5 \times 10^{-5}$ sec. and $\tau_s = 8 \times 10^{-3}$ sec. (depending on age), we therefore obtain $D_f = 3 \times 10^{-7}$ cm$^2$/sec. and $D_s = 2 \times 10^{-9}$ cm$^2$/sec.

As is known in the art, the quantities $D_f$ and $D_s$ can be interpreted in terms of molecular phenomena expected to contribute to increased light scattering within the ocular lens. In particular, $D_f$ can be identified with the rapidity of diffusion expected for the largest of the relatively small, unaggregated protein species within the lens, the $\alpha$-crystallins. In contrast, $D_s$ is over 100 times smaller than $D_f$ and therefore corresponds to the diffusion of much larger entities. This is consistent with the findings of numerous biochemical and in vitro scattering studies, showing that with age and cataractogenesis, large aggregates of protein form in the lens. Such aggregates have been found to range in molecular weight from about $10^7$ to $2 \times 10^8$ grams/mole, at least 10 to 200 times the largest typical weights observed for native proteins isolated from the lens, the $\alpha$-crystallins.

In contrast to previous work on light scattering from the ocular lens, it has been found to be necessary to include the effect of scattering from substantially immobile scatterers in the analysis of the autocorrelation functions. The necessity for this term was realized by first carrying out the analysis with $F_{imm} = 0$. In this case, we found that the best fit values of the parameters could not in general provide a good fit to the value of the correlation function at the delayed point at $\tau = 5.1$ milliseconds. As it is physically reasonable to expect that very large aggregates of protein diffusing quite slowly, as well as cell membranes and cytoskeletal elements could contribute to the scattering, the functions were then reanalyzed using equation (4) with $F_{imm}$ incorporated as a fitted parameter. In this case, we found that the delayed point was well fit in general. A statistically significant reduction in the mean sum of squared residual errors, within individual correlation functions, was obtained by using $F_{imm}$ as a fitted parameter.

Using the fitted values $F_{imm}$ and $F_{mos}$, the amounts of light $I_{imm}$, $I_{mos}$ and $I_{mof}$ scattered by each of the three types of scatterers represented in equation (4) can be calculated. These are given by $I_{imm} = I_{tot} F_{imm}$, $I_{mos} = I_{tot}(1 - F_{imm}) F_{mos}$ and $I_{mof} = I_{tot}(1 - F_{imm})(1 - F_{mos})$. With use of these quantities, the origin of changes in total intensity, $I_{tot}$, such as those associated with aging, can be traced to changes in each of the types of scattering present.

Thus, it can be readily recognized that the information obtained from the autocorrelation function provides several quantitative and complementary measures of the phenomenon of association and aggregation of proteins within the lens. First, the formation of large aggregates of the proteins will in general lead to an increase of the quantity $I_{tot}(140)$, as measured directly. Second, as aggregates form the amount of the light which is scattered by slow mobile aggregates, $I_{mos}$, or by substantially immobile material, $I_{imm}$, will in general increase. Third, growth in the average size of aggregates will in general led to a decrease in their associated diffusivity $D_S$.

Those skilled in the art will recognize, or be able to ascertain, using no more than routine experimentation, many equivalents to the specific embodiment of the invention described herein. For example, the delivery, observation, control and collection optics are not intended to be solely limited to the embodiments described herein, but rather are intended to extend to any optical system suitable for these purposes. One skilled in the art will readily appreciate that there are a number of algebraically equivalent forms for the model correlation function presented herein. Such equivalents are intended to be encompassed by the following claims.

What is claimed is:

1. A method for in vivo detection of cataractogenesis in ocular tissue, comprising the steps of:
   (a) producing a light;
   (b) causing said light to impinge on the ocular tissue;
   (c) collecting light that is scattered from the ocular tissue, the scattered light having a fluctuating intensity;
   (d) performing a correlation analysis on said fluctuating intensity to produce a signature containing a component representing the intensity of the light scattered by substantially immobile scatterers in a non-constant fashion; and
   (e) determining a degree of cataractogenesis from said signature.

2. The method of claim 1 wherein step (d) comprises computing a temporal autocorrelation function of said intensity fluctuations.

3. The method of claim 2 wherein step (d) further comprises performing a least squares analysis on the temporal autocorrelation function to determine the functional form of the function $C(\tau)$ which best fits the temporal autocorrelation function, where $$C(\tau) = \alpha[I_{mof}e^{-\tau/\tau_f} + I_{imm}]^2 + [I_{tot}]^2,$$

where $\tau$ is a time delay variable, $\alpha$ denotes an amplitude to baseline ratio, $I_{mof}$ represents the intensity of light scattered by mobile, fast diffusing scatterers, $I_{mos}$ represents the intensity of light scattered by mobile, slowly diffusing scatterers, $I_{imm}$ represent the intensity of light scattered by light scatterers which diffuse very slowly in comparison to said mobile scatterers, $\tau_f$ and $\tau_s$ are time constants that characterize the fast and slowly diffusing scatterers, respectively, and $I_{tot}$ denotes the total, average intensity of scattered light.

4. The method of claim 2 wherein step (d) further comprises performing a least squares analysis on the temporal autocorrelation function to determine the functional form of the function $C(\tau)$ which best fits the temporal autocorrelation function, where $$C(\tau) = \alpha B\{(1-F_{imm})[(1-F_{mos})e^{-\tau/\tau_f} + F_{mos}e^{-\tau/\tau_s}] + F_{imm}\}^2 + B,$$

where $\tau$ is a time delay variable, $\alpha$ denotes an amplitude to baseline ratio, B denotes a baseline value, $F_{mos}$ denotes the fraction of light intensity scattered by mobile scatterers which is associated with slowly diffusing scatterers, $F_{imm}$ denotes the fraction of total light intensity scattered due to light scatterers which diffuse very slowly in comparison to said mobile scatterers, and $\tau_f$ and $\tau_s$ are time constants that characterize the fast and slowly diffusing scatterers, respectively.

5. A method for in vivo detection of cataractogenesis in ocular tissue, comprising the steps of:
   (a) producing a light;
   (b) causing said light to impinge on the ocular tissue;
   (c) collecting light that is scattered from the ocular tissue, the scattered light having a fluctuating intensity;
   (d) performing a correlation analysis on said fluctuating intensity to produce a signature containing a non-constant component representing the intensity of the light scattered by immobile scatterers in the ocular tissue, said immobile scatterers being substantially immobile in the ocular tissue relative to mobile scatterers; and
   (e) determining a degree of cataractogenesis from said signature.

6. The method of claim 5 wherein step (d) comprises computing a temporal autocorrelation function of said intensity fluctuations.

7. The method of claim 5 wherein step (d) further comprises performing a least squares analysis on the temporal autocorrelation function to determine the functional form of the function $C(\tau)$ which best fits the temporal autocorrelation function, where $$C(\tau) = \alpha[I_{mof}e^{-\tau/\tau_f} + I_{mos}e^{-\tau/\tau_s} + I_{imm}]^2 + [I_{tot}]^2,$$

where $\tau$ is a time delay variable, $\alpha$ denotes an amplitude to baseline ratio, $I_{mof}$ represents the intensity of light scattered by mobile, fast diffusing scatterers, $I_{mos}$ represents the intensity of light scattered by mobile, slowly diffusing scatterers, $I_{imm}$ represent the intensity of light scattered by light scatterers which diffuse very slowly in comparison to said mobile scatterers, $\tau_f$ and $\tau_s$ are time constants that characterize the fast and slowly diffusing scatterers, respectively, and $I_{tot}$ denotes the total, average intensity of scattered light.

8. The method of claim 5 wherein step (d) further comprises performing a least squares analysis on the temporal autocorrelation function to determine the functional form of the function $C(\tau)$ which best fits the temporal autocorrelation function, where $$C(\tau) = \alpha B\{(1-F_{imm})[(1-F_{mos})e^{-\tau/\tau_f} + F_{mos}e^{-\tau/\tau_s}] + F_{imm}\}^2 + B,$$

where $\tau$ is a time delay variable, $\alpha$ denotes an amplitude to baseline ratio, B denotes a baseline value, $F_{mos}$ denotes the fraction of light intensity scattered by mobile scatterers which is associated with slowly diffusing scatterers, $F_{imm}$ denotes the fraction of total light intensity scattered due to light scatterers which diffuse very slowly in comparison to said mobile scatterers, and $\tau_f$ and $\tau_s$ are time constants that characterize the fast and slowly diffusing scatterers, respectively.

9. An apparatus for in vivo detection of cataractogenesis in ocular tissue, comprising:
   a light source to produce light that impinges on the ocular tissue with some of said impinging light being scattered by scattering elements within the ocular tissue;
   a light detector constructed to detect light that is scattered from the ocular tissue wherein said scattered light has a fluctuating intensity;
   an analyzer coupled to said light detector to perform correlation analysis on said detected light to produce a signature containing a component representing the intensity of the light scattered by substantially immobile scatterers in the ocular tissue in a non-constant fashion; and means coupled to said analyzer for determining a degree of cataractogenesis from said signature.

10. The apparatus of claim 9 wherein said analyzer comprises an autocorrelator computing a temporal autocorrelation function of said intensity fluctuations.

11. The apparatus of claim 9 wherein said analyzer is further constructed to compute a temporal autocorrelation function of said intensity fluctuations and performs a least squares analysis on said temporal autocorrelation function to determine the functional form of the function $C(\tau)$ which best fits said temporal autocorrelation function, where $$C(\tau) = \alpha[I_{mof}e^{-\tau/\tau_f} + I_{mos}e^{-\tau/\tau_s} + I_{imm}]^2 + [I_{tot}]^2,$$

where $\tau$ is a time delay variable, $\alpha$ denotes an amplitude to baseline ratio, $I_{mof}$ represents the intensity of light scattered by mobile, fast diffusing scatterers, $I_{mos}$ represents the intensity of light scattered by mobile, slowly diffusing scatterers, $I_{imm}$ represent the intensity of light scattered by light scatterers which diffuse very slowly in comparison to said mobile scatterers, $\tau_f$ and $\tau_s$ are time constants that characterize the fast and slowly diffusing scatterers, respectively, and $I_{tot}$ denotes the total, average intensity of scattered light.

12. The apparatus of claim 9 wherein said analyzer is further constructed to compute a temporal autocorrelation function of said intensity fluctuations and performs a least squares analysis on said temporal autocorrelation function to determine the functional form of the function $C(\tau)$ which best fits said temporal autocorrelation function, where $$C(\tau) = \alpha B\{(1 - F_{imm})[(1 - F_{mos})e^{-\tau/\tau_f} + F_{mos}e^{-\tau/\tau_s}] + F_{imm}\}^2 + B,$$

where $\tau$ is a time delay variable, $\alpha$ denotes an amplitude to baseline ratio, B denotes a baseline value, $F_{mos}$ denotes the fraction of light intensity scattered by mobile scatterers which is associated with slowly diffusing scatterers, $F_{imm}$ denotes the fraction of total light intensity scattered due to light scatterers which diffuse very slowly in comparison to said mobile scatterers, and $\tau_f$ and $\tau_s$ are time constants that characterize the fast and slowly diffusing scatterers, respectively.

13. An apparatus for in vivo detection of cataractogenesis in ocular tissue, comprising:

a light source to produce a light that impinges on the ocular tissue with some of said impinging light being scattered by scattering elements within the ocular tissue;

a light detector to detect at least a portion of the light that is scattered from the ocular tissue wherein said scattered light has a fluctuating intensity;

an analyzer coupled to said light detector to perform correlation analysis on said detected light to produce a signature containing a non-constant component representing the intensity of the light scattered by immobile scatterers, said immobile scatterers being substantially immobile in the ocular tissue relative to mobile scatterers; and means for determining a degree of cataractogenesis from said signature.

14. The apparatus of claim 13 wherein said analyzer comprises an autocorrelator computing a temporal autocorrelation function of said intensity fluctuations.

15. The apparatus of claim 13 wherein said analyzer is further constructed to compute a temporal autocorrelation function of said intensity fluctuations and performs a least squares analysis on the temporal autocorrelation function to determine the functional form of the function $C(\tau)$ which best fits the temporal autocorrelation function, where $$C(\tau) = \alpha[I_{mof}e^{-\tau/\tau_f} + I_{mos}e^{-\tau/\tau_s} + I_{imm}]^2 + [I_{tot}]^2,$$

where $\tau$ is a time delay variable, $\alpha$ denotes an amplitude to baseline ratio, $I_{mof}$ represents the intensity of light scattered by mobile, fast diffusing scatterers, $I_{mos}$ represents the intensity of light scattered by mobile, slowly diffusing scatterers, $I_{imm}$ represent the intensity of light scattered by light scatterers which diffuse very slowly in comparison to said mobile scatterers, $\tau_f$ and $\tau_s$ are time constants that characterize the fast and slowly diffusing scatterers, respectively, and $I_{tot}$ denotes the total, average intensity of scattered light.

16. The apparatus of claim 13 wherein said analyzer is further constructed to compute a temporal autocorrelation function of said intensity fluctuations and performs a least squares analysis on the temporal autocorrelation function to determine the functional form of the function $C(\tau)$ which best fits the temporal autocorrelation function, where $$C(\tau) = \alpha B\{(1 - F_{imm})[(1 - F_{mos})e^{-\tau/\tau_f} + F_{mos}e^{-\tau/\tau_s}] + F_{imm}\}^2 + B,$$

where $\tau$ is a time delay variable, $\alpha$ denotes an amplitude to baseline ratio, B denotes a baseline value, $F_{mos}$ denotes the fraction of light intensity scattered by mobile scatterers which is associated with slowly diffusing scatterers, $F_{imm}$ denotes the function of total light intensity scattered due to light scatterers which diffuse very slowly in comparison to said mobile scatterers, and $\tau_f$ and $\tau_s$ are time constants that characterize the fast and slowly diffusing scatterers, respectively.

* * * * *

UNITED STATES PATENT AND TRADEMARK OFFICE
CERTIFICATE OF CORRECTION

PATENT NO. : 5,427,095
DATED : June 27, 1995
INVENTOR(S) : George M. Thurston, Douglas L. Hayden and George B. Benedek It is certified that error appears in the above-indentified patent and that said Letters Patent is hereby corrected as shown below:

On the cover page, item [73], please delete "Massachusetts Institute of Technology Oculon Corporation, Cambridge, Mass." and substitute therefore --Oculon Corporation; Massachusetts Institute of Technology, Cambridge, Mass.--.

In column 11, claim 3, line 41, please delete "$C(\tau)=\alpha[I_{mof}e^{-t/\tau f}+I_{imm}]^2+I_{tot}]^{2}$", and substitute therefore -- $C(\tau)=\alpha[I_{mof}e^{-t/\tau f}+I_{mos}e^{-\tau/\tau s}+I_{imm}]^2+[I_{tot}]^2$--.

In column 13, claim 11, line 20, please delete "αdenotes" and substitute therefore --α denotes--.

In column 13, claim 12, lines 39 and 40, please *delete* "$C(\tau)=\alpha B\{(1-F_{imm})[(1-F_{mos})e^{-t/\tau f}+F_{mos}e^{-t/\tau f}+F_{mos}e^{-\tau/\tau s}]+F_{imm}\}^2+B,$" and substitute therefore -- "$C(\tau)=\alpha B\{(1-F_{imm})[(1-F_{mos})e^{-t/\tau f}+F_{mos}e^{-\tau/\tau s}]+F_{imm}\}^2+B,$--.

In column 14, claim 16, line 46, please delete "αdenotes" and substitute therefore --α denotes--.

In column 14, claim 16, line 50, please delete "function" and substitute therefore --fraction--.

Signed and Sealed this

Second Day of January, 1996

*Attest:*

BRUCE LEHMAN

*Attesting Officer*    Commissioner of Patents and Trademarks

UNITED STATES PATENT AND TRADEMARK OFFICE
CERTIFICATE OF CORRECTION

PATENT NO. : 5,427,095
DATED : June 27, 1995
INVENTOR(S) : George M. Thurston, et al.

It is certified that error appears in the above-indentified patent and that said Letters Patent is hereby corrected as shown below:

Column 1, line 5-10:
Following the title and before the heading "TECHINICAL FIELD", please insert the following:

—*This invention was made with government support under Grant No. NIH-5R01-EY05127 by the National Institutes of Health. The government has certain rights in the invention.*—

Signed and Sealed this

Twenty-sixth Day of March, 1996

*Attest:*

BRUCE LEHMAN

*Attesting Officer*     Commissioner of Patents and Trademarks